United States Patent [19]

Panster et al.

[11] 4,442,040

[45] Apr. 10, 1984

[54] POLYMERIC RHODIUM, IRIDIUM AND RUTHENIUM PHOSPHINE COMPLEX COMPOUNDS, PROCESSES FOR THEIR PRODUCTION AND USE

[75] Inventors: Peter Panster; Peter Kleinschmit, both of Hanau, Fed. Rep. of Germany

[73] Assignee: Degussa Aktiengesellschaft, Frankfurt am Main, Fed. Rep. of Germany

[21] Appl. No.: 283,868

[22] Filed: Jul. 16, 1981

[30] Foreign Application Priority Data

Aug. 5, 1980 [DE] Fed. Rep. of Germany ....... 3029599

[51] Int. Cl.$^3$ .............................................. C07F 15/00
[52] U.S. Cl. ............................. 260/429 R; 260/429 J; 528/15
[58] Field of Search ........................ 260/429 R, 429 J; 528/15

[56] References Cited

U.S. PATENT DOCUMENTS

| | | | |
|---|---|---|---|
| 2,856,837 | 12/1974 | Chandra | 260/429 R |
| 3,726,809 | 4/1973 | Allum et al. | 260/429 R UX |
| 3,832,404 | 8/1974 | Allum et al. | 260/429 R X |
| 4,134,906 | 1/1979 | Oswald et al. | 260/429 R X |

*Primary Examiner*—Helen M. S. Sneed
*Attorney, Agent, or Firm*—Beveridge, DeGrandi & Kline

[57] ABSTRACT

The invention relates to complex compounds of rhodium, iridium or ruthenium with a silicic acid-like structure with a least one phosphine ligand, the trivalent phosphorus of which is bonded to silicon via at least one divalent organic residue, the remaining three valences of the silicon building, via oxygen bridges arising from the hydrolysis of functional substituents originally bound there, a inter- or intra-molecularly crosslinked polycondensate. The required charge equalization is effected by an anion. Also disclosed are processes for recovery of the polymeric complexes and their use in heterogeneous catalysis of various chemical reactions.

24 Claims, No Drawings

POLYMERIC RHODIUM, IRIDIUM AND RUTHENIUM PHOSPHINE COMPLEX COMPOUNDS, PROCESSES FOR THEIR PRODUCTION AND USE

The invention relates to polymeric coordination compounds of rhodium, iridium and ruthenium with silicon substituted phosphines as ligands, processes for their production and the use of these heterogeneous metal complexes as catalysts.

So-called homogeneous catalysts, which are present in the same phase as the reactant and substrate during the catalysis process, substantially possess the advantage, as against purely heterogeneous catalysts, of consistently higher activity and also higher selectivity, and apart from this permit access to new products to a greater extent. However, greater process-technical difficulties as a rule arise with their use in connection with their separation from the product formed and also from solvent present. The recovery of the usually expensive noble metal components from the sumps of the reaction solution is also expensive and is normally possible only with large losses of noble metal. A further disadvantage of homogeneous catalysts is their frequently only short useful life, due to the tendency, always present in solution, to form catalytically inactive coordination compounds.

In order to overcome the disadvantages of use of homogeneous catalysts and to unite the advantages of both kinds of catalysts, those of the homogeneous ones and those of the heterogeneous ones, in a new type of catalyst, homogeneous catalysts have already for some time been bound, by way of covalent, ionogenic or even absorptive alternate action, to carriers. The state of the art in this sector or catalysis has previously been described in numerous review articles, e.g. also by Z. M. Michalska and D. E. Webster in CHEMTECH February 1975, p. 117 or by R. H. Grubbs in CHEMTECH August 1977, p. 512. Organic polymers were here principally used until now as carrier materials, and are partially made suitable for fixation of homogeneous catalysts only after a suitable modification, e.g., in the case of polystyrene by primary introduction of chloromethyl groups. The heterogenization of metallic complexes by use of organic polymers is described, e.g., by R. H. Grubbs and L. C. Kroll in J. Amer. Chem. Soc. 93, 3062 (1971), by M. Čapka, P. Svoboda, M. Černý and J. Hetflejš in Tetrahedron Letters 1971, 4787 and also in British Pat. No. 1,277,737.

The organic polymers used as carrier materials generally fulfill the requirements which are imposed on carriers for purely heterogeneous catalysts, but only in a very limited manner: they possess no definite structure. Their conformation, and hence surface, and also the volume of the individual particles, depends strongly on external parameters such as temperature, pressure and solvent. Swelling of the carrier in the solvent used is always important, in order to permit penetration of the substrate and reactant to the catalytic centers, and to allow the reaction velocity not to be controlled by diffusion. The high mobility of the matrix also permits fixed metallic units to come together, so that formation of catalytically inactive multinuclear complexes is made possible and, besides this, uncoordinated ligands can block the catalytically active metallic center (cf. G. Strukul, P. D'Olimpio, M. Bonivento, F. Pinna and M. Graziani in J. Mol. Catal. 2, 179 (1977)). The case can also occur that dissolving out of the polymeric organic matrix into the solvents results, which would per se be advantageous for the catalytic reaction.

In contrast to this, inorganic polymer systems such as, e.g., precipitated or pyrogenic silicic acids, possess a definite structure; the fixed metallic units are situated at the surface and are thus more easily accessible by the substrate and reactant. Apart from this, their temperature and ageing resistance is higher by far than that of the organic polymers. It thus appears understandable that inorganic carriers have already been utilized for fixation of homogeneous catalysts. Examples of this are, among others, described in U.S. Pat. No. 4,083,803, DE-OS No. 2,062,351, or by F. Wild, G. Gubitosa and H. H. Brintzinger in J. Organomet. Chem. 148, 73 (1978). Of course, inorganic carrier materials possess a severe disadvantage insofar as the number of hydroxyl groups by which binding to the ligand or to the metal atom can be completed is relatively small, so that a high loading with ligands or metal atoms can result and much carrier ballast is transported around with the fixed catalyst.

Recently, as described in DE-OS No. 2,834,691, a method hitherto not yet put into practice could be found, according to which the homogeneous rhodium sulfide complex catalysts can be heterogenized without the use of a carrier. The polymeric carrier, built up of intra- and inter-molecularly formed siloxane units, is here produced by hydrolysis and condensation of the trialkoxy, triphenoxy, or trihalosilyl units present in a proportion of two per sulfide ligand. The silicic-acid-like solid formed in a quantitative extent by this polycondensation has the composition to be expected after splitting off the functional groups; its chemical behavior and the IR-spectroscopic properties confirm that the structure of the rhodium complex units was substantially not altered by the heterogenization. The matrix of these polymeric rhodium sulfide catalysts also shows, as expected, the above-mentioned good properties of inorganic carriers and apart from this can be quasi tailor-made, e.g. in respect of the important aspect that more or fewer ligands are required than according to the stoichiometry of the complex to be heterogenized, or so-called crosslinking agents can be built in, by means of which control of the density of catalytic centers in the solid is possible. In contrast to homogeneous catalysts bound to inorganic carriers, the polymers have above all, however, the advantages of being able to have a high noble metal concentration at the same ligand:metal ratio, being simply accessible preparatively, and being resistant to alkali hydroxides due to the strongly hydrophobic character of the matrix.

It has now been possible to find that not only polymeric rhodium sulfide complexes, but also very catalytically active polymeric rhodium-phosphine, iridium-phosphine, and ruthenium-phosphine complexes are synthesizable according to this concept of polycondensation with ligands substituted with trifunctional silicon. It was also completely surprisingly found that with a suitable structure of the metallic complex, a single trifunctional silicon group per phosphine ligand is in principle quite sufficient to transform the phosphine complex thus formed into a polymeric, insoluble form. These new polymeric phosphine complexes of rhodium, iridium and ruthenium are therefore characterized in that at least one phosphine of the general formula (I)

 (1)

is coordinatively bound to the metallic central atom, an atomic noble metal:phosphorus ratio of 1:1–1:10^6 is present, the coordination positions which in appropriate circumstances are still free are occupied by other electron pair donors, such as, e.g., carbon monoxide, nitric oxide, triphenylphosphine, triphenylarsine, phosphite, amine, sulfide, olefin, acetylene, nitrile, isonitrile, cyanate, isocyanate or water, and the necessary charge equalization is completed by an inorganic or organic anion, such as chloride, bromide, iodide, nitrate, acetylacetonate, acetate, trifluoroacetate, trichloroacetate, propionate, methoxide, ethoxide, propoxide, butoxide, phenoxide, tetraphenylborate, hexafluorophosphate, methyl, ethyl, propyl, butyl, phenyl or perfluorophenyl ion, in appropriate circumstances with complete or partial replacement of such anions by hydrogen ion, where in formula (1) $R^1$ stands for a group of general formula (2):

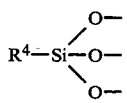

in which $R^4$ furthermore stands for a straight-chain or branched alkylene group with 1 to 10 C atoms, for a cycloalkylene group with 5 to 8 C atoms, and for units of the following type:

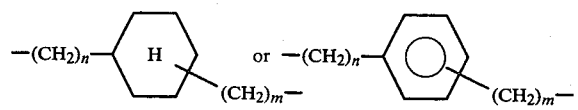

in which n is the number, between 1 and 6, of methylene groups situated on phosphorus, m can be a number from 0 through 6, and the ring H atoms can be partially or completely replaced by halogen, methyl or ethyl, and the free valences on the oxygen atoms are saturated either by silicon atoms of further units of formula (2) or by built-in silicon, titanium, or aluminum bridge atoms which arise from the hydrolysis products of the cross-linking agents tetraalkoxysilicate (e.g., $Si(OC_2H_5)_4$, $Si(OCH_3)_4$, tetraalkoxytitanate (e.g., $Ti(OCH_3)_4$, $Ti(OC_2H_5)_4$), trialkoxyaluminum compounds (e.g., $Al(OCH_3)_3$, $Al(OC_2H_5)_3$), or tetrahalides of silicon or titanium or trihalides of aluminum; $R^2$ and $R^3$ can have the same meaning as $R^1$, stand for an alkyl or alkoxy group containing 1 to 6 C atoms, or for a phenyl or phenoxy group which in appropriate circumstances is substituted with alkyl or alkoxy groups, and both have the same or different meaning.

The monomeric precursors of these phosphines of formula (1) are compounds which are known in principle and can be produced by efficient processes, e.g. as described in German Patentschrift No. 1,118,781 or in DE-OS No. 2,062,351. Examples of monomeric precursors of the usable phosphines are:

$(C_6H_5)_2P(CH_2)_2Si(OCH_3)_3$,
$(C_6H_5)_2P(CH_2)_5Si(OC_2H_5)_3$,

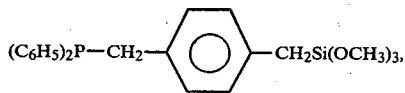

$(p—CH_3—C_6H_4)_2P—(CH_2)_3Si(OC_2H_5)_3$,
$(C_6H_5)_2P(CH_2)_3—SiCl_3$ $(C_6H_5)P[(CH_2)_3Si(OC_2H_5)_3]_2$,
$(C_6H_5O)P[(CH_2)_3Si(OCH_3)_3]_2$, $P[(CH_2)_3Si(OC_2H_5)_3]_3$, $(C_2H_5)P[(CH_2)_3Si(OC_6H_5)_3]_2$

The composition of the transition metal complexes produced by use of the phosphine ligands of general formula (1) can predominantly be described, in the case of rhodium, by the general formulas:

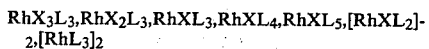

and in the case of the iridium and ruthenium complexes can be predominantly described by the general formulas:

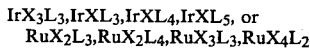

where L represents at least one ligand of formula (1), and otherwise has the range of meaning stated above, and X stands for one of the anions previously cited.

Particularly preferred are the polymeric complex compounds of the stoichiometric composition $RhX_3L_3$, $RhX_2L_3$, $RhXL_4$, $RhXL_5$, $RhXL_3$, $IrX_3L_3$, and $RuX_2L_3$, which are best able to be produced directly from the monomeric complex precursors and hence possess the character of starting compounds, and in which L furthermore stands for at least one ligand of formula (1), X stands for chloride, bromide, iodide, hydride, nitrate, acetate, methoxide, ethoxide, propoxide, butoxide, phenoxide, perchlorate, tetraphenylborate or hexafluorophosphate. The other types of complexes set out above can be obtained after first partially chemically modifying the initial polymers, which can or must be carried out under the aspect of a further improvement of the activity or selectivity of the heterogenized homogeneous catalyst. The chemical alteration consists either of the reduction of the degree of oxidation of the metallic atom, of the introduction of another anion X, or of the introduction of a further, not matrix-bound ligand, such as, e.g., triphenylphosphine. In practice this means a reaction of the polymers with, e.g., $H_2$, CO, or $H_2$ plus CO at total pressures of 1–3,000 bar and temperatures of room temperature through 350° C. or a reaction with usual reducing agents, such as, e.g., formaldehyde, hydrazine, alkali or alkaline earth metal borohydride, borane compounds, aluminum hydrides, aluminum alkyls, or also only alcohols or a reaction with Lewis acids such as aluminum alkyls, or the introduction of another anion, e.g., by means of alkali metal alkoxides such as alkali metal methoxide, ethoxide, propoxide, alkali metal phenoxides or alkali metal alkyls or phenyls or by means of sodium acetate, acetylacetonate, or iodide, or a reaction with additional ligands such as triphenylphosphine, triphenylarsine, amine, sulfide, or even olefin or diolefin.

The composition of the polymers is not limited to the preceding formulas, but also not only fewer, but also more, phosphine ligands L of formula than the stoichiometry of the above transition metal types sets as maximum possible can also be used. In the polymers there can therefore be present atomic Rh:P-, Ir:P- and Ru:P- ratios of 1:1 to 1:10$^6$, as mentioned.

Two independent methods of production of these polymeric rhodium, iridium and ruthenium phosphine complex compounds, insoluble in organic solvents, are also objects of the invention. The one process is in detail characterized in that complex compounds of the stoichiometric composition RhX$_3$L$_3'$, RhX$_2$L$_3'$, RhXL$_4'$, RhXL$_5'$, RhXL$_3'$, IrX$_3$L$_3'$ and RuX$_2$L$_3'$, in which L' can stand for at least one ligand representing a monomeric precursor of a phosphine according to formulas (1) and (2) and otherwise for another electron pair donor (such as carbon monoxide, nitric oxide, triphenylphosphine, triphenylarsine, phosphite, amine, sulfide, olefin, diolefin, acetylene, nitrile, isonitrile, cyanate, isocyanate or water) and X is the inorganic or organic anion, are first conventionally produced in situ in a solvent or solvent mixture of preferably polar nature (such as methanol, ethanol, propanol, butanol, dioxan, nitromethane, ethyleneglycol monomethyl ethyl, ethylene glycol dimethyl ether, diethylene glycol dimethyl ether, ethylene glycol, acetone, tetrahydrofuran, dimethyl formamide, dimethyl sulfoxide, benzene, toluene, cyclohexane, methyl cyclohexane, n-hexane, chloroform, methylene chloride or mixtures of these), in appropriate circumstances at elevated temperature and in appropriate circumstances also in the presence of an excess of the monomeric precursor of a phosphine according to formulas (1) and (2) over the stoichiometry of the above complex compounds, and simultaneously or subsequently is reacted with water or an aqueous acid solution, if necessary after a change or solvent and/or an addition of crosslinking agents such as Si(OCH$_3$)$_4$, Si(OC$_2$H$_5$)$_4$, Ti(OCH$_3$)$_4$, Ti(OC$_2$H$_5$)$_4$, Al(OCH$_3$)$_3$, Al(OC$_2$H$_5$)$_3$, or the tetrahalides of silicon or titanium or the trihalides of aluminum, at or preferably below the boiling temperature of the solvent used, and possibly with simultaneous or subsequent distillative removal of the alcohol or phenol arising, and hence polycondensed; the solid polycondensate is treated in suspension, preferably at elevated temperature, and is then freed from solvent by distillation, filtration, centrifugation or decantation and then washed or extracted with the same or another solvent, subsequently dried at temperatures of 80°-350° C. and finally, if required, mechanically comminuted.

The other process consists in detail in that the ligands representing a monomeric precursor of a phosphine according to formulas (1) or (2) and bearing at least two trifunctional, hydrolyzable silicon groups per molecule is reacted with water without, or preferably with, the use of a solvent, such as, among others, also used in the preceding method, possibly with simultaneous or subsequent distillative removal of the alcohol or phenol arising, and at room temperature or elevated temperature; the solid thus formed is reacted, directly or after prior isolation and also drying, with ligands which contain halogen, nitrate, acetate, propionate and/or hydrides and in appropriate circumstances are easily displaceable, such as rhodium, iridium or ruthenium compounds bearing water of crystallization, carbon monoxide, amine, triphenylphosphine, phosphite, sulfide, olefin, acetylene, nitrile, isonitrile, cyanate or isocyanate, in appropriate circumstances with displacement of one of these ligands; the solid polycondensate is treated in suspension, preferably at elevated temperature, is then freed of solvent by distillation, filtration, centrifugation or decantation and is then washed or extracted with the same or another solvent, subsequently dried at temperatures of 80°-350° C. and finally, if required, is mechanically comminuted.

Suitable solvents which can be used for the in situ preparation of the monomeric complex precursors and their polycondensation or the primary polycondensation of the phosphine ligand and the subsequent reaction of the polymeric ligand with the above rhodium, iridium and ruthenium compounds are preferably methanol, ethanol, propanol, butanol, dioxan, nitromethane, ethylene glycol monomethyl ether, ethylene glycol dimethyl ether, diethylene glycol dimethyl formamide, dimethyl sulfoxide, benzene, toluene, cyclohexane, methyl cyclohexane, n-hexane, chloroform, methylene chloride or mixtures of these solvents. Polar solvents are however preferred. The polycondensation as a rule occurs spontaneously, with formation of a voluminous precipitate, after the addition of a given amount of water or aqueous acid solution to the solution of the monomers. In appropriate circumstances, the volatile byproducts formed in this reaction, such as alcohols, phenols, etc., are simultaneously or subsequently separated by distillation, thereby furthering the polycondensation. The solid is now treated in suspension for a time, preferably at elevated temperature, and is then freed of solvent by distillation, filtration, centrifugation or decantation, washed or extracted with the same or another solvent, dried for a few hours to days at temperatures of 80°-350° C., if necessary with the use of vacuum, and finally, insofar as it is required, mechanically comminuted.

The above explanations can also be described, for example, by the following reaction equations:

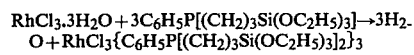

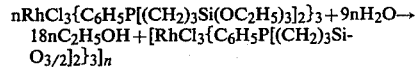

or

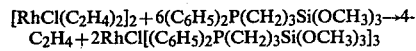

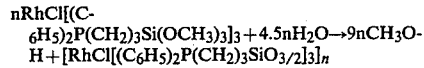

As an alternative to this two-stage process method, in some cases excess water or aqueous acid solution can also be added to the solvent previously used in the in situ preparation of the monomeric complex compound, since the phosphine substituted with trifunctional silicon can be polycondensed better in the coordinated than in the uncoordinated state because of its steric arrangement in the complex, so that the desired polymeric, insoluble coordination compound precipitates quantitatively in the course of the reaction.

Influence on the surface and particle structure of the polymers can be exerted by the kind of preparative process and its parameters. This specific surfaces of 1-1,000 m$^2$/g can be adjusted.

In some cases it is found to be advantageous, in the sense of an accelerated polycondensation, to add to the precipitation solution, after or before addition of the water, a small amount of already existing polymeric product as a condensation seed and/or a small amount of a catalyst, such as aqueous mineral acid.

According to the second of the two possible processes, which envisages the primary polycondensation of the phosphine substituted with at least two trifunctional silicon atoms and a subsequent reaction of the polycondensate with a complex bearing an easily displaceable ligand, the solid formed after the polycondensation can be made to react directly, with a stoichiometry such that atomic Rh:P ratios of 1:1 to 1:10$^6$ are present in the product formed, with rhodium, iridium or ruthenium compounds bearing ligands which contain hydride and/or which represent salts of a hydrogen halide acid, nitric acid, or a lower carboxylic acid and/or which are in appropriate circumstances easily displaceable, such as water, carbon monoxide, amine, triphenylphosphine, phosphite, sulfide, olefin, diolefin, acetylene, nitrile, isonitrile, cyanate, or isocyanate, without isolation, extraction and drying, in the already provided solvent (mixture), preferably in suitable solvents at room temperature or elevated temperature, which can even in appropriate circumstances lie above the reflux temperature of the solvent used. Further processing occurs analogously to the first process variants.

As already mentioned, the polymeric starting compounds of formulas $RhX_3L_3$, $RhX_2L_3$, $RhXL_4$, $RhXL_5$, $RhXL_3$, $IrX_3L_3$ and $RuX_2L_3$ can be converted by a chemical modification into other polymeric complex compounds of rhodium, iridium, or ruthenium respectively, so that an optimal system as regards activity and selectivity can be prepared in relation to their use as catalysts. For this purpose, the polymer is preferably suspended in a solvent and reacted with the modifying agent below room temperature or at room temperature up to 350° C., at pressures of 1–3,000 bar. The choice of solvent is not particularly critical here; it should only satisfy two conditions; inertness with respect to both reaction participants, and the modifying agent must be soluble in it. This modification of the polymer can either take place directly during use of the catalyst, or the suspension of the modified polymer can be fed directly, without further operating stages, to the application. The treated solid can, however, also be separated from the solvent, washed and finally dried.

The polymeric coordination compounds of rhodium, iridium and ruthenium according to the invention represent valuable catalysts for chemical reactions, such as hydroformylation, hydrogenation, oligomerization, addition of CO to a triple bond, carboxymethylation, and isomerization reactions and also for reactions of CO with $H_2$.

Thus for example, the hydroformylation of olefins with use of the new rhodium-containing catalysts can be carried out in a manner known per se at hydrogen/carbon monoxide total pressures of 1–1,000 bar and temperatures of from room temperature up to 250° C., with or without use of a solvent, high catalyst selectivity permitting the exclusive production of aldehydes or of corresponding alcohols.

A hydrogenation of olefinic compounds can be carried out at room temperature or elevated temperature, at reduced pressure, atmospheric pressure, or superatmospheric pressure.

Here the heterogenized catalysts according to the invention show activities comparable to those of analogous homogeneous systems, but they possess, as against the latter, the advantages of a much longer catalyst life and an easier separability from components of the reaction mixture such as solvent, substrate residues and the product.

The heterogenized catalyst according to the invention can be isolated from the reaction mixtures by the usual separation methods such as decantation, centrifugation or filtration without a loss of activity being detectable, and without noble metal compounds being detectable to any considerable extent in the liquid phase.

The invention is further illustrated below with reference to examples of embodiments. The special phosphine ligands L of formula (1) used according to the invention in the individual complex systems according to the invention in these examples represent simple and easily accessible representatives of their class and hence possess the character of models. This statement is justified, in particular, by the generally known properties of silicon-organic compounds of this type and also by the fact that the phosphine ligands of the new complexes are not substantially altered with respect to their ligand qualities, i.e., the coordination possibilities of the phosphorus atom, as against the state of the art as described at the beginning. An analogical conclusion to the further species L which can be used within the scope of the invention is therefore justified, as will be obvious to anyone skilled in the art. Of course, the corresponding statement holds for the anion X used.

EXAMPLE 1

A clear solution of 2.7 g (10.25 mMol) $RhCl_3.3H_2O$ in 80 ml dry ethanol was treated within 15 minutes at room temperature with 12.8 g (29.45 mMol) $(C_6H_5)P[(CH_2)_3Si(OCH_3)_3]_2$, dissolved in 40 ml ethanol. The mixture was then stirred for 2.5 hr under reflux. The solution was then cooled to room temperature and 5 ml water were added within about 10 min. The precipitated, orange-yellow precipitate was further stirred for a further 2 h at reflux temperature, filtered from the liquid and extracted with ethanol for 4 h. After drying for 4 hours at 80° C. in oil pump vacuum, 10.8 g (99.3% of theoretical) rhodium-containing solid were obtained. On complete hydrolysis and precipitation, the following analytical values are to be expected:

|  | Rh % | Cl % | P % | C % | H % |
| --- | --- | --- | --- | --- | --- |
| Theory | 9.70 | 10.03 | 8.39 | 39.03 | 4.64 |
| Found | 9.61 | 9.45 | 7.86 | 38.20 | 5.72 |

EXAMPLE 2

To a solution of 1.9 g (7.22 mMol) $RhCl_3.3H_2O$ in 60 ml dried ethanol were added dropwise 5.07 g (14.55 mMol) of $(C_6H_5)_2P(CH_2)_3Si(OCH_3)_3$, diluted with 20 ml ethanol. On stirring for 2.5 hr under reflux, a clear lightening of the reaction mixture, which was at first red, was observed. Finally, 5 ml of water were added to this in the course of 10 min. A voluminous yellow precipitate formed already after the first few drops. The suspension was heated for a further 30 min under reflux; the solid was then filtered off, extracted with 4 ml toluene and dried at 80° C. and $10^{-1}$ mbar for 4 hr. Yield: 5.57 g (99.9% of theoretical).

Analytical values:

|  | Rh % | Cl % | P % | C % | H % |
|---|---|---|---|---|---|
| Theory | 13.33 | 13.77 | 8.08 | 47.02 | 4.21 |
| Found | 12.27 | 12.37 | 6.51 | 46.51 | 4.29 |

EXAMPLE 3

1.16 g (3.21 mMol) $IrCl_3.3.5\ H_2O$ were partially dissolved in 30 ml ethanol. 5.0 g (9.64 mMol) of $(C_6H_5)P[(CH_2)_3Si(OC_2H_5)_3]_2$, diluted with 10 ml ethanol, were added dropwise to this suspension during 10 min. The mixture was heated to reflux temperature and kept at this temperature for a further 2½ hours. After this time, 6 ml of desalted water was dropped into the clear brown solution during 10 min. A gel-like paste then gradually formed. This was stirred for a further 3 hr at the reflux temperature of the solvent and then transferred to an extraction sleeve, freed from soluble residues by 4-hour extraction, and finally dried for 4 hr at 80° C. and $10^{-1}$ mbar. Yield: 3.70 g (97.0% of theoretical).

Analytical values:

|  | Ir % | Cl % | P % | C % | H % | Si % |
|---|---|---|---|---|---|---|
| Theory | 16.18 | 8.95 | 7.82 | 36.40 | 4.33 | 14.19 |
| Found | 15.79 | 8.80 | 7.29 | 35.95 | 4.50 | 14.01 |

EXAMPLE 4

0.545 g (1.64 mMol) $RhCl_3(CH_3CN)_3$ were united with 5.10 g $(C_6H_5)P[(CH_2)_3Si(OC_2H_5)_3]_2$ in 70 ml dry toluene at room temperature. The clear solution which gradually formed was first heated for 2 hr under reflux. 5 ml of desalted water were then dropped into it during about 10 min. The mixture was stirred for a further 30 min at boiling temperature, and a toluene/$H_2O$/ethanol azeotrope was then distilled off with a simultaneous intensification of the formation of precipitate in the flask. After completion of azeotrope removal there first followed separation, then a 4-hr extraction with ethanol of the solid formed and finally drying for 3 hr at 100° C. and $10^{-1}$ mbar. 3.16 g (96.9% of theoretical) could be obtained, the composition of which, according to the analytical data given below can be described by the approximate molecular formula $RhCl_3\{P[(CH_2)_3SiO_{3/2}]_2C_6H_5\}_6$. Specific surface determination according to the BET method gave a value of 250 m²/g.

Analytical values:

|  | Rh % | Cl % | C % | H % | P % |
|---|---|---|---|---|---|
| Theory | 5.18 | 5.35 | 43.51 | 5.17 | 9.35 |
| Found | 4.86 | 4.92 | 43.83 | 5.60 | 9.39 |

EXAMPLE 5

To a cold solution of 4.83 g (14.54 mMol) $RhCl_3(CH_3CN)_3$ in 140 ml of dried toluene was added the 2.5-fold molar amount (12.67 g, approx. 36.35 mMol) of $(C_6H_5)_2P—CH_2\ CH_2CH_2Si(OCH_3)_3$, dissolved in 20 ml dried toluene, in portions. The solution was stirred for 3 hr at boiling temperature, then cooled to room temperature; 7.57 g (36.35 mMol) $Si(OC_2H_5)_4$ were then added as crosslinking agent, and finally 15 ml of distilled water were slowly dropped in. The suspension of the orange-yellow precipitate thus formed was then stirred for 1 hr at room temperature, then dried by removal of the solvent in a high vacuum.

The solid residue was transferred to an extraction sleeve and extracted for 4 hr with toluene containing 1% water, then dried at 120° C. and $10^{-1}$ mbar. Yield: 15.1 g (98.2% of theoretical). On completion of formation of the desired polycondensate of molecular formula $RhCl_3\{P(CH_2)_3—SiO_{3/2}(C_6H_5)_2\}_{2.5}.(SiO_2)_{2.5}$, the following analytical values were to be expected:

Analytical values:

|  | Rh % | Cl % | P % | C % | H % |
|---|---|---|---|---|---|
| Theory | 9.73 | 10.05 | 7.32 | 42.58 | 3.81 |
| Found | 9.81 | 9.48 | 6.80 | 41.72 | 3.92 |

EXAMPLE 6

From 6.2 g (15.10 mMol)

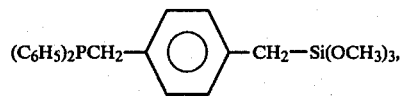

1.67 g (5.03 mMol) $RhCl_3(CH_3CN)_3$ and 6.29 g (30.20 mMol) of $Si(OC_2H_5)_4$, analogously to Example 5, 7.91 g (98.65% of theoretical) of

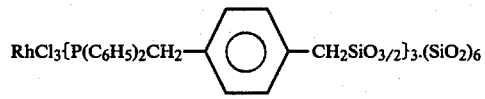

were obtained.
Analytical values:

|  | Rh % | Cl % | P % | C % | H % |
|---|---|---|---|---|---|
| Theory | 6.46 | 6.67 | 5.83 | 45.21 | 3.41 |
| Found | 6.24 | 6.32 | 5.71 | 44.95 | 3.52 |

EXAMPLE 7

653.5 mg (2.39 mMol) $RhCl_3.3.67\ H_2O$ were dissolved in 25 ml ethanol and 3.0 g (7.17 mMol) $(C_6H_5)_2P(CH_2)_5Si(OC_2H_5)_3$, dissolved in 10 ml ethanol, were added dropwise. The greenish brown solution was stirred for 3 hr at room temperature and 5 ml $H_2O$, acidified with 0.1 ml of 0.1 N HCl, were then added.

After a further 1 hr of stirring, the solvent was distilled off under vacuum; the remaining solid was stirred for 2 hr in a mixture of 50 ml of monoethylene glycol dimethyl ether and 10 ml $H_2O$ at reflux temperature and then extracted for 4 hr with the same solvent mixture. After drying for 3 hr at 120° C. and $10^{-1}$ mbar, 2.4 g (91.8% of theoretical) of a brown, fine powder were obtained, the analytical data for which agreed well with the theoretically expected molecular formula $RuCl_2\{(C_6H_5)_2P(CH_2)_5SiO_{3/2}\}_3$.

Analytical values:

|  | Rh % | Cl % | P % | C % | H % |
|---|---|---|---|---|---|
| Theory | 9.24 | 6.48 | 8.49 | 55.98 | 5.53 |
| Found | 9.14 | 6.90 | 8.56 | 55.01 | 5.48 |

EXAMPLE 8

1.66 g (4.27 mMol) [RhCl(C$_2$H$_4$)$_2$]$_2$ were suspended in 80 ml toluene. To the suspension heated to 90° C. there were added dropwise 11.13 g (25.61 mMol) (C$_6$H$_5$)P[(CH$_2$)$_3$Si(OCH$_3$)$_3$]$_2$, diluted with 10 ml toluene. The mixture was stirred for 3 hr at the same temperature, and a clear brown solution was gradually obtained. 10 ml of desalted water were then dropped in, and stirring was continued for a further hour at reflux temperature. The contents of the flask were then brought to dryness, kept at 130° C. for 2 hr, extracted for 4 hr with monoethylene glycol dimethyl ether and dried for 4 hr at 100° C. and 10$^{-1}$ mbar. The complex of theoretical formula RhCl {P[(CH$_2$)$_3$SiO$_{3/2}$]$_2$(C$_6$H$_5$)}$_3$, weighing 7.4 g (84.3% of theoretical) in the final product, possessed the following analytical data:

Analytical values:

|  | Rh % | Cl % | P % | C % | H % |
|---|---|---|---|---|---|
| Theory | 10.01 | 3.45 | 9.04 | 42.08 | 5.00 |
| Found | 9.88 | 3.36 | 8.87 | 40.99 | 5.07 |

EXAMPLE 9

A mixture of 50 g (96.38 mMol) C$_6$H$_5$P[(CH$_2$)$_3$Si(OC$_2$H$_5$)$_3$]$_2$ and 50 ml ethanol was heated to 70° C., and 50 ml of H$_2$O were then added dropwise. The polycondensate thus formed was stirred under reflux for a further 2 hr, then filtered off using a pressure filter, washed with an ethanol/H$_2$O mixture, and then dried at 150° C. and 100 mbar. The polymeric solid with the theoretical molecular formula C$_6$H$_5$P[(CH$_2$)$_3$SiO$_{3/2}$]$_2$ possessed the following analytical data:

Analytical values:

|  | P % | C % | H % |
|---|---|---|---|
| Theory | 10.45 | 48.63 | 5.78 |
| Found | 9.95 | 47.92 | 5.81 |

Yield: 28.5 g (99.8% of theoretical).

EXAMPLE 10

10 g (33.74 mMol) of the polymeric phosphine prepared as in Example 9 and 0.444 g (1.69 mMol) RhCl$_3$.3H$_2$O were united in 100 ml ethanol. The suspension was stirred for 24 hr at room temperature and then filtered by means of an extraction sleeve. The solid remaining in the sleeve was extracted for 4 hr with ethanol and then dried at 150° C. and 100 mbar.

The yellow-colored solid, which should have the theoretical molecular formula RhCl$_3${(C$_6$H$_5$)P[(CH$_2$)$_3$SiO$_{3/2}$]$_2$}$_{20}$, possessed the following analytical data:

Analytical values:

|  | Rh % | Cl % | P % |
|---|---|---|---|
| Theory | 1.68 | 1.73 | 10.09 |
| Found | 1.49 | 1.54 | 10.01 |

EXAMPLE 11

Analogously to Example 10, from 1.245 g (2.82 mMol) [Rh(O$_2$CCH$_3$)$_2$]$_2$ and 4.54 g (16.90 mMol) C$_6$H$_5$P[(CH$_2$)$_2$SiO$_{3/2}$]$_2$ there were obtained 5.7 g of product of composition Rh(O$_2$CCH$_3$)$_2${C$_6$H$_5$P[(CH$_2$)$_2$SiO$_{3/2}$]$_2$}$_3$ with the following analytical data:

Analytical values:

|  | Rh % | P % | C % | H % | Si % |
|---|---|---|---|---|---|
| Theory | 10.03 | 9.06 | 39.80 | 4.42 | 16.42 |
| Found | 10.39 | 9.21 | 38.91 | 4.56 | 16.83 |

EXAMPLE 12

1.5 g of a polymeric rhodium catalyst, prepared according to Example 1, of molecular formula RhCl$_3${C$_6$H$_5$P[(CH$_2$)$_3$—SiO$_{3/2}$]$_2$}$_3$ were suspended in 30 ml n-butanol. During 1 hr, a solution of 672.7 mg of Na n-butoxide, dissolved in 30 ml n-butanol, was dropped in at a temperature of 80° C. The suspension was stirred for a further 3 hr at 80° C. and then filtered off. The remaining solid was washed three times with 20 ml portions of methanol and finally dried at 180° C. and 10$^{-1}$ mbar. The Rh content of the red-brown solid was 8.21%.

EXAMPLE 13

50.14 mg of the catalyst modified according to Example 12 and with a content of 8.21% Rh (approx. 0.04 mg-atom Rh), 4.36 ml (40 mMol) of ethyl acrylate, and 20 ml of toluene were united in a 50 ml glass flask which was connected to a glass hydrogenation apparatus. After saturation of the solution with hydrogen, the ethyl acrylate was quantitatively hydrogenated to ethyl propionate within 90 min at 80° C., under a H$_2$ pressure of less than 1 bar and with magnetic stirring. The average H$_2$ uptake velocity was about 10 ml/min. The catalyst was then filtered off under a N$_2$ atmosphere and used for a new hydrogenation analogous to that just described. The hydrogenation was ended this time after 85 min. corresponding to an average H$_2$ uptake of about 11 ml/min.

EXAMPLE 14

A mixture of 535 mg of the polymeric catalyst (9.61% Rh) obtained according to Example 1, 62.5 ml hexene-1, and 180 ml toluene was exposed in a 500 ml lifting autoclave to a cold pressure of CO/H$_2$ (1:1) of 200 bar. Within 60 min. at a temperature of 125° C., about 97.5% of the hexene-1 used was converted to n-heptanal and 2-methyl-hexanal. The composition was determined by gas chromatography to be about 55% n-heptanal, 42.5% 2-methylhexanal and about 2.5% n-hexene.

After the catalyst was filtered off, it was again used, analogously to the above description, for hydroformylation of hexene-1. Within 30 min., at a temperature of 100° C., about 98% of the 1-hexene utilized was converted to about 60% n-heptanal and about 40% 2-methylhexanal.

EXAMPLE 15

40.48 ml methanol (1 mol) and 283.9 mg (2 mMol) of CH$_3$I, dissolved in 50 ml of toluene, and 250 mg of the catalyst prepared as in Example 1, were exposed in a 300 ml steel autoclave with magnetic stirring to a CO cold pressure of 30 bar. At a temperature of 100° C. and with topping up of the CO used for 2 hours, about 93% of the methanol utilized was converted within 24 hours. 45% methyl acetate and 55% acetic acid were formed. The dark red catalyst was filtered off and used again in an analogous manner, without a change in its catalytic activity being detectable.

EXAMPLE 16

40.48 ml methanol (1 mol) and 283.9 mg (2 mMol) of CH$_3$I, dissolved in 50 ml toluene, and 243 mg of the iridium catalyst prepared according to Example 3 and of molecular formula IrCl$_3${C$_6$H$_5$P[(CH$_2$)$_3$SiO$_{3/2}$]$_2$}$_3$ (15.8% Ir) were reacted as in Example 15 with CO. After 10 hr, 40% of the methanol utilized was converted into acetic acid (15%) and methyl acetate (85%).

Further modification and variations of the invention will be apparent to those skilled in the art from reading the foregoing and are intended to be encompassed by the claims appended hereto.

We claim:

1. A polymeric complex compound of a noble metal selected from the group consisting of rhodium, iridium and ruthenium, having a silica-like structure, wherein at least one phosphine of the formula:

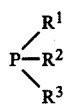 (1)

is coordinately bound to the noble metal atom selected from the group consisting of rhodium, iridium and ruthenium; an atomic ratio of noble metal to phosphorus being 1:1–1:10$^6$; any free coordination positions on said noble metal atom being occupied by other electron pair donors, and any required charge equalization being furnished by an inorganic or organic anion; wherein R$^1$ is a group of the formula:

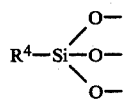 (2)

in which R$^4$ is a straight-chain or branched alkylene with 1 to 10 carbons, cycloalkylene with 5 to 8 carbons, or a group of the following formula:

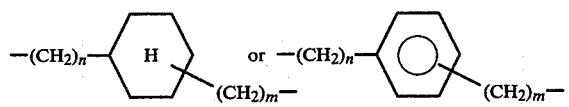

in which n is from 1 to 6, and corresponds to the number of methylene groups situated on phosphorus, m can be a number from 0 through 6, the ring hydrogen atoms can be partially or completely substituted by halogen, methyl or ethyl, and the free valences on the oxygen atoms are saturated either by silicon atoms of further units of formula (2) or by silicon, titanium or aluminum bridging atoms, R$^2$ and R$^3$ may be R$^1$, alkyl or alkoxy containing 1 to 6 carbons, phenyl or phenoxy groups substituted with alkyl or alkoxy of 1 to 6 carbons.

2. A polymeric complex compound according to claim 1, with a stoichiometric composition represented by the group consisting of:

RhX$_3$L$_3$, RhX$_2$L$_3$, RhXL$_4$, RhXL$_5$, RhXL$_3$, IrX$_3$L$_3$ and RuX$_2$L$_3$ in which
L is a ligand corresponding to the phosphines of the formula (1)
and X is chloride, bromide, iodide, hydride, nitrate, acetate, methoxide, ethoxide, propoxide, butoxide, phenoxide, perchlorate, tetraphenylborate, or hexafluorophosphate.

3. A complex compound according to claim 1, treated with H$_2$, CO, or H$_2$ plus CO or with reducing agents or with Lewis acids or by introduction of another anion or by reaction with additional ligands at total pressures of 1–3,000 bar and temperatures below room temperature or from room temperature up to 350° C.

4. A process for the production of a polymeric compound, insoluble in organic solvents, of a noble metal selected from the groups consisting of rhodium, iridium and ruthenium as defined in claim 1, comprising:
forming by an in situ reaction in a solvent, a complex compound of the stoichiometric composition selected from the group consisting of:

RhX$_3$L$_3$', RhX$_2$L$_3$', RhXL$_4$', RhXL$_5$', RhXL$_3$', IrX$_3$L$_3$' and RuX$_2$L$_3$' in which
L' is at least one ligand representing a monomeric precursor of a phosphine of formulae (1) and (2), or another electron pair donor,
and X is the inorganic or organic anion,
thereafter reacting with water or aqueous acid solution, for a polycondensation reaction to form a polycondensate,
treating the solid polycondensate in suspension to remove solvent, and subsequently drying.

5. The process of claim 4, wherein the solvent for the in situ reaction is a polar solvent.

6. The process of claim 4, wherein the said reacting is carried out at elevated temperatures.

7. The process of claim 4, wherein the said reacting is carried out in the presence of an excess monomeric precursor of formulae (1) and (2).

8. The process of claim 4, wherein a cross-linking orthosilicate-, orthotitanate- or aluminum trioxi-member is present in the reaction.

9. The process of claim 4, wherein the reaction is followed by distillation to remove an ROH product.

10. The process of claim 8, wherein the cross-linking agent is Si(OCH$_3$)$_4$, Si(OC$_2$H$_5$)$_4$, Ti(OCH$_3$)$_4$, Ti(OC$_2$H$_5$)$_4$, Al(OCH$_3$)$_3$, Al(OC$_2$H$_5$)$_3$ or the tetrahalides of silicon or titanium or the trihalides of aluminum.

11. The process of claim 10, wherein the reaction is carried out at or below the boiling point of the solvent.

12. The process of claim 4, wherein the solid polycondensate is removed from solvent by distillation, filtration, centrifugation or decanting followed by washing or extraction with a solvent.

13. The process of claim 4, wherein the drying is carried out at 80°–350° C.

14. The process of claim 4, wherein comminution of the resulting product is carried out.

15. A process for the production of a polymeric complex compound of a noble metal selected from the group consisting of rhodium, iridium and ruthenium as defined in claim 1, the complex compound being soluble with difficulty in organic solvents comprising:
reacting at least one ligand bearing at least two trifunctional, hydrolyzable silicon groups per molecule and representing a monomeric precursor of a phosphine according to formulae (1) or (2) with water, and thereafter reacting the solid thus formed with a rhodium, iridium or ruthenium ionic compound containing, if appropriate, easily replaceable ligands, the polycondensate obtained thereby then being treated in suspension to remove solvent, and then washing said polycondensate, and subsequently drying.

16. The process of claim 15, wherein the reaction with water is carried out with the addition of a solvent.

17. The process of claim 15, wherein the process is carried out with recovery of the ROH product.

18. The process of claim 15, wherein the solid recovered after the condensation reaction with water is isolated and dried and then reacted with the noble metal ligand.

19. The process of claim 15, wherein the polycondensate product is subjected to distillation, filtration, centrifugation or decantation to remove the solvent.

20. The process of claim 15, wherein the polycondensate product is washed with another solvent.

21. The process of claim 15, wherein the polycondensate is dried at 80°–350° C.

22. The process of claim 15, wherein the polycondensate is comminuted after drying.

23. A process according to claims 4 or 15, wherein the polymeric complex compound, preferably suspended in a solvent, is after-treated with $H_2$, CO, or $H_2$ plus CO or with reducing agents or with Lewis acids or by introduction of another anion or by reaction with additional ligands, at total pressures of 1–3,000 bar temperatures below room temperature or from room temperature up to 350° C.

24. A polymeric complex compound according to claim 1, wherein said other election pair donors are selected from the group consisting of carbon monoxide, nitric oxide, triphenylphosphine, triphenylarsine, phosphite, amine, sulfide, olefin, acetylene, nitride, isonitride, cyanate, isocyanate and water and said inorganic or organic anion for charge equalization is selected from the group consisting of chloride, bromide, iodide, nitrate, acetylacetonate, acetate, trifluoroacetate, trichloroacetate, propionate, methoxide, ethoxide, propoxide, butoxide, phenoxide, tetraphenylborate, hexafluorophosphate, methyl, ethyl, propyl, butyl, phenyl and perfluorophenyl.

* * * * *